US006953138B1

(12) United States Patent
Dworak et al.

(10) Patent No.: US 6,953,138 B1
(45) Date of Patent: Oct. 11, 2005

(54) SURGICAL STAPLER ANVIL WITH NESTED STAPLE FORMING POCKETS

(75) Inventors: Bruce E. Dworak, Cromwell, CT (US); Frank W. Dworak, 329 Pleasant Valley Rd., Rocky Hill, CT (US) 06067

(73) Assignee: Frank W. Dworak, Rocky Hill, CT (US)

( * ) Notice: Subject to any disclaimer, the term of this patent is extended or adjusted under 35 U.S.C. 154(b) by 11 days.

(21) Appl. No.: 10/782,151

(22) Filed: Feb. 18, 2004

(51) Int. Cl.$^7$ .......................... A61B 17/04; A61B 17/10
(52) U.S. Cl. .................. 227/175.1; 227/19; 227/181.1; 227/154; 227/155
(58) Field of Search ............................... 227/175.1, 19, 227/181.1, 154, 155

(56) References Cited

U.S. PATENT DOCUMENTS

| | | | |
|---|---|---|---|
| 3,490,675 A | 1/1970 | Green et al. | 227/19 |
| 3,494,533 A | 2/1970 | Green et al. | 227/19 |
| 3,499,591 A | 3/1970 | Green | 227/76 |
| 4,589,582 A | 5/1986 | Bilotti | 227/19 |
| 4,767,044 A | 8/1988 | Green | 227/19 |
| 4,805,823 A | 2/1989 | Rothfuss | 227/19 |
| 5,040,715 A | 8/1991 | Green et al. | 227/176 |
| 5,111,987 A | 5/1992 | Moeinzadeh et al. | 227/180 |
| 5,221,036 A | 6/1993 | Takase | 227/19 |
| 5,258,009 A | 11/1993 | Conners | 606/219 |
| 5,350,400 A | 9/1994 | Esposito et al. | 606/219 |
| 5,415,334 A | 5/1995 | Williamson, IV et al. | 227/178 |
| 5,480,089 A | 1/1996 | Blewett | 227/175.1 |
| 5,487,500 A | 1/1996 | Knodel et al. | 227/181.1 |
| 5,505,363 A | 4/1996 | Green et al. | 227/175.1 |
| 5,562,241 A | 10/1996 | Knodel et al. | 227/175.1 |
| 5,597,107 A | 1/1997 | Knodel et al. | 227/175.2 |
| 5,630,540 A | 5/1997 | Blewett | 227/176.1 |
| 5,662,258 A | 9/1997 | Knodel et al. | 227/175.1 |
| 5,732,871 A | 3/1998 | Clark et al. | 227/175.1 |
| 5,735,848 A | 4/1998 | Yates et al. | 606/48 |
| 5,749,896 A | 5/1998 | Cook | 606/219 |
| 5,762,255 A | 6/1998 | Chrisman et al. | 227/175.2 |
| 5,814,055 A * | 9/1998 | Knodel et al. | 606/151 |
| 5,820,009 A | 10/1998 | Melling et al. | 227/176.1 |
| 5,911,353 A * | 6/1999 | Bolanos et al. | 227/180.1 |
| 5,941,442 A | 8/1999 | Geiste et al. | 227/175.1 |
| 6,010,054 A | 1/2000 | Johnson et al. | 227/176.1 |
| 6,131,790 A | 10/2000 | Piraka | 227/176.1 |
| 6,241,139 B1 | 6/2001 | Milliman et al. | 227/175.1 |
| 6,669,073 B2 * | 12/2003 | Milliman et al. | 227/175.2 |
| 6,817,508 B1 * | 11/2004 | Racenet et al. | 227/176.1 |

* cited by examiner

Primary Examiner—Rinaldi I. Rada
Assistant Examiner—Brian Nash
(74) Attorney, Agent, or Firm—Alix, Yale & Ristas, LLP (57) ABSTRACT

A surgical stapler anvil provides an expanded leg-receiving target area for a staple forming pocket in a compact staggered array by narrowing the lateral width of the leg-clinching portion of a laterally adjacent pocket. Advantageously, the lateral spacing between adjacent rows of staple forming pockets can remain small, while the leg-receiving target area for laterally adjacent rows of pockets is significantly expanded. The staple forming pockets include two mirror image leg-forming cups. The cups are longitudinally aligned with their respective ascending leg clinching portions adjoining in the center of the pocket. Laterally spaced guide surfaces extend upwardly and outwardly from the clinching surface at the bottom of the cup to define an expanded leg-receiving target area at the distal ends of the pocket. Substantially planar laterally outward portions of the guide surface intersect with the guide surface of a laterally adjacent pocket to form a non-linear ridge.

30 Claims, 7 Drawing Sheets

SURGICAL STAPLER ANVIL WITH NESTED STAPLE FORMING POCKETS

BACKGROUND OF THE INVENTION

1. Field of the Invention

The invention relates to surgical staplers, and more particularly to anvils for use in surgical staplers of the type in which one or more staples are driven through body tissue and against an anvil to form and clinch the staple legs and thereby secure the tissue.

2. Description of the Related Art

Surgical staplers having a wide variety of configurations are known. Generally, the tissue to be secured is positioned between a staple holding assembly and an opposing anvil assembly. One or more generally U-shaped staples are driven from the staple holding assembly, through the tissue, and against the anvil to bend the ends of the staple legs back toward the base of the staple. The formed and clinched staple secures the tissue. Many surgical staplers include staple holding assemblies and anvils configured to drive and form one or more rows of closely spaced staples. In staplers of this general type, it is important that every staple be formed properly since an incompletely or improperly formed staple may leave a gap in a wound closure.

It is conventional to provide separate staple forming pockets for each staple in the staple in the row or rows. It is necessary to maintain relatively stringent alignment between the staple holding assembly and the anvil to assure that the staples enter the pockets correctly for proper clinching. The importance of maintaining good alignment between the relatively movable staple holding assembly and anvil assembly may contribute to the complexity of the instrument and to the cost of manufacturing and maintaining it.

A further complicating factor is presented by the nature of the tissue through which the staples will be driven. Some tissues may include tough or fibrous parts that can deflect the staple legs from their intended path. A deflected staple leg may miss its forming pocket, resulting in a malformed or incompletely clinched staple.

One way to increase the amount of tolerance in a surgical staple and still ensure proper staple leg entry into the forming pockets is to provide an enlarged target area for the staple legs. As shown in FIGS. 1–4, U.S. Pat. No. 5,480,089 discloses a surgical staple forming anvil 100 in which each pocket 102 is provided with channeling surfaces 104 disposed about the distal ends of each leg-forming cup to present an enlarged target area for the staple legs. The channeling surfaces 104 are angled to direct each staple leg toward clinching surfaces 106 at the bottom of the pocket 102. The anvil 100 has a flat upper surface 103 extending between laterally and longitudinally adjacent staple forming pockets 102. The channeling surfaces 104 disclosed in the '089 patent are conical surfaces having an angular orientation θ relative to the upper surface 103 that is smaller than the angular orientation of the staple clinching surfaces 106 at the bottom of the pocket 102.

Figure 1:
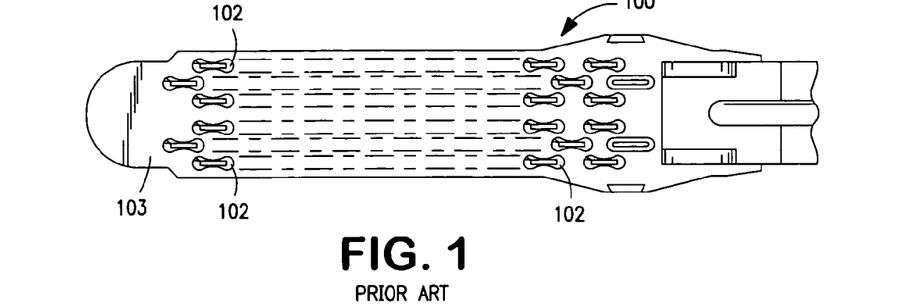
FIGS. 1–4 are plan, perspective and sectional views through a prior art surgical stapler anvil.
Figure 2:
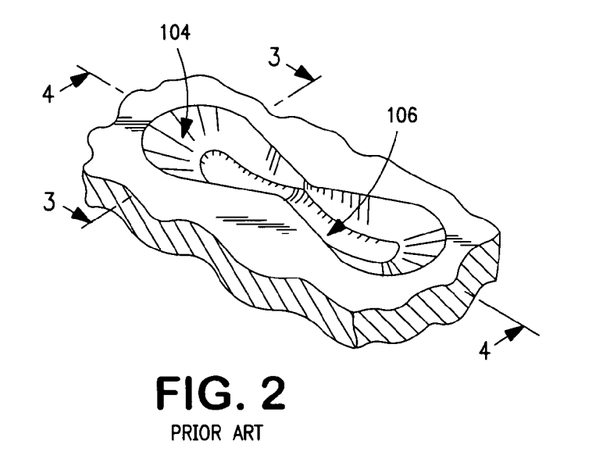
Figure 3:
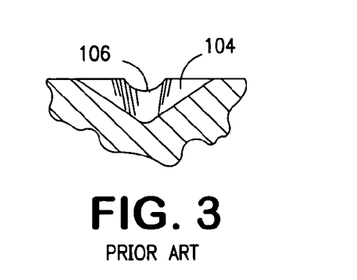
Figure 4:
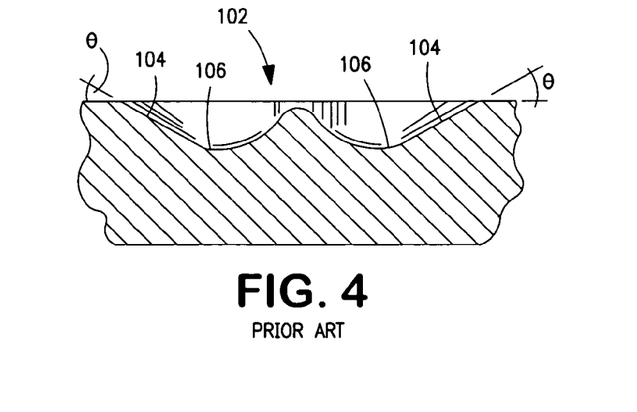
Figure 5:
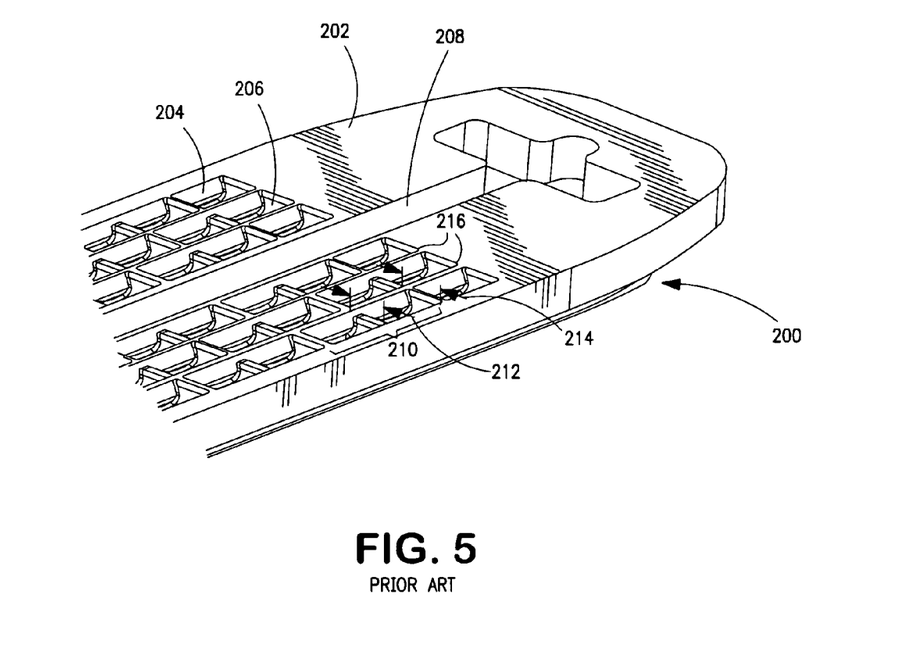
FIG. 5 is a partial perspective view of an alternative prior art surgical stapler anvil configuration.

FIG. 5 illustrates an alternative surgical stapler anvil with a more densely packed array of staple forming pockets. The anvil 200 defines three parallel rows of staggered staple forming pockets 210. Channeling surfaces 204 are provided to enlarge the target area for the staple legs. The lateral width 212 of the staple clinching portion (longitudinally in the center) of each pocket 210 is the same as the lateral width 214 of the leg-receiving portion (at the distal ends of the pocket 210). The anvil 200 of FIG. 5 is configured for use in a surgical stapler which applies three parallel staggered rows of surgical staples while simultaneously cutting the tissue with a blade moving in slot 208. The anvil 200 defines three staggered rows of staple forming pockets along either side of the blade slot 208. Each of the staple forming pockets is principally defined by arcuate clinching surfaces 206 and substantially planar angled guide surfaces 204. The anvil of FIG. 5 replaces the compound curved pocket surfaces illustrated in FIGS. 1–4 with arcuate clinching surfaces 206 that are substantially flat in cross-section and planar guide surfaces 204. The clinching surface 206 extends continuously from a descending leg-receiving end portion of the staple forming pocket to an ascending, centrally located leg-clinching portion of the pocket. The compact pocket array arranged in staggered rows of FIG. 5 leaves no planar anvil surface 202 surrounding or between the pockets. It can be seen that the pockets are arranged in longitudinally aligned rows such that the guiding surfaces of pockets of one row meet the guiding surfaces of pockets in an adjacent row to form a linear ridge 216, separating the rows of pockets from each other.

The compound arcuate channeling surfaces disclosed in the '089 patent, while effective, are difficult to form in a cost-effective manner. The pocket array of FIG. 5 is configured without the difficult to form compound arcuate surfaces. It would be beneficial to provide a surgical stapler anvil having a compact array of staple forming pockets, where each pocket presents an expanded target area for the staple legs. It would also be beneficial if such a compact array of staple forming pockets could be produced by a coining process.

While the prior art pocket arrays illustrated in FIGS. 1–5 have been generally effective, further improvements in function and cost efficient production are possible.

SUMMARY OF THE INVENTION

Briefly stated, a surgical stapler anvil according to aspects of the present invention expands the leg-receiving portion of staple forming pockets in a compact staggered array by narrowing the lateral width of the leg-clinching portion of a laterally adjacent pocket. In this manner, the lateral spacing between adjacent rows of staple forming pockets can remain small, while the leg-receiving target area for at least a central row of pockets is expanded. The invention recognizes that the central leg-clinching surfaces of the pocket do not benefit from an increased lateral width in the same way as the leg-receiving portions of the pocket. By taking lateral width from the leg-clinching portion of an adjacent pocket, the lateral width of a leg-receiving portion can be expanded beyond what was possible in previous compact arrays of staple forming pockets.

Staple forming pockets according to aspects of the present invention include two mirror image leg-forming cups. Each leg-forming cup includes a descending leg-receiving portion and an ascending leg clinching portion. The cups are longitudinally aligned with their respective ascending leg clinching portions adjoining in the center of the pocket. The bottom surface of each leg-forming cup is defined by an arcuate clinching surface. Laterally spaced guide surfaces extend upwardly and outwardly from the clinching surface to define an expanded leg-receiving target area at the distal ends of the pocket. Each guide surface includes an initial steeply angled portion defining the lateral sides of the clinching surface at the bottom of the cup. A radius defines a transition from the steeply angled surface to a more shallowly angled, substantially planar laterally outward portion of the guide surface. This substantially planar portion of the guide surface intersects with the guide surface of an adjacent pocket to form a non-linear ridge.

The relatively simple surface shapes used to form the nested pockets allow the use of cold metal forming techniques. In particular, the planar and arcuate surface shapes lend themselves to efficient production of dies for stamping or more particularly coining the arrays of nested pockets.

An object of the present invention is to provide a new and improved surgical stapler anvil in which the leg-receiving portions of the staple forming pockets are enlarged to improve the reliability of staple formation and allow a loosening of manufacturing tolerances for the stapler.

Another object of the present invention is to provide a new and improved surgical stapler anvil in which the leg-receiving portion of the staple forming pockets are expanded while maintaining a compact lateral spacing between adjacent rows of staple forming pockets.

A further object of the present invention is to provide a new and improved surgical stapler anvil having expanded leg-receiving portions of the staple forming pockets where the pocket configurations are compatible with production by coining.

BRIEF DESCRIPTION OF THE DRAWINGS

These and other objects, features, and advantages of the present invention will become readily apparent to those skilled in the art upon reading the description of the preferred embodiment, in conjunction with the accompanying drawings in which.

DETAILED DESCRIPTION OF AN EXEMPLARY EMBODIMENT

An exemplary embodiment of a surgical stapler anvil with nesting pockets will now be described with reference to FIGS. 6–12. FIG. 12 illustrates an exemplary surgical stapler anvil 40 configured for use in a surgical stapler which simultaneously cuts tissue while applying three staggered rows of surgical staples through tissue along either side of the incision. The pockets 10 in each row 42 are longitudinally offset from the pockets in an adjacent row such that the leg-receiving portions 12 of the pockets in one row are laterally adjacent to the leg-clinching portions 14 of the pockets in an adjacent row.

Figure 6:
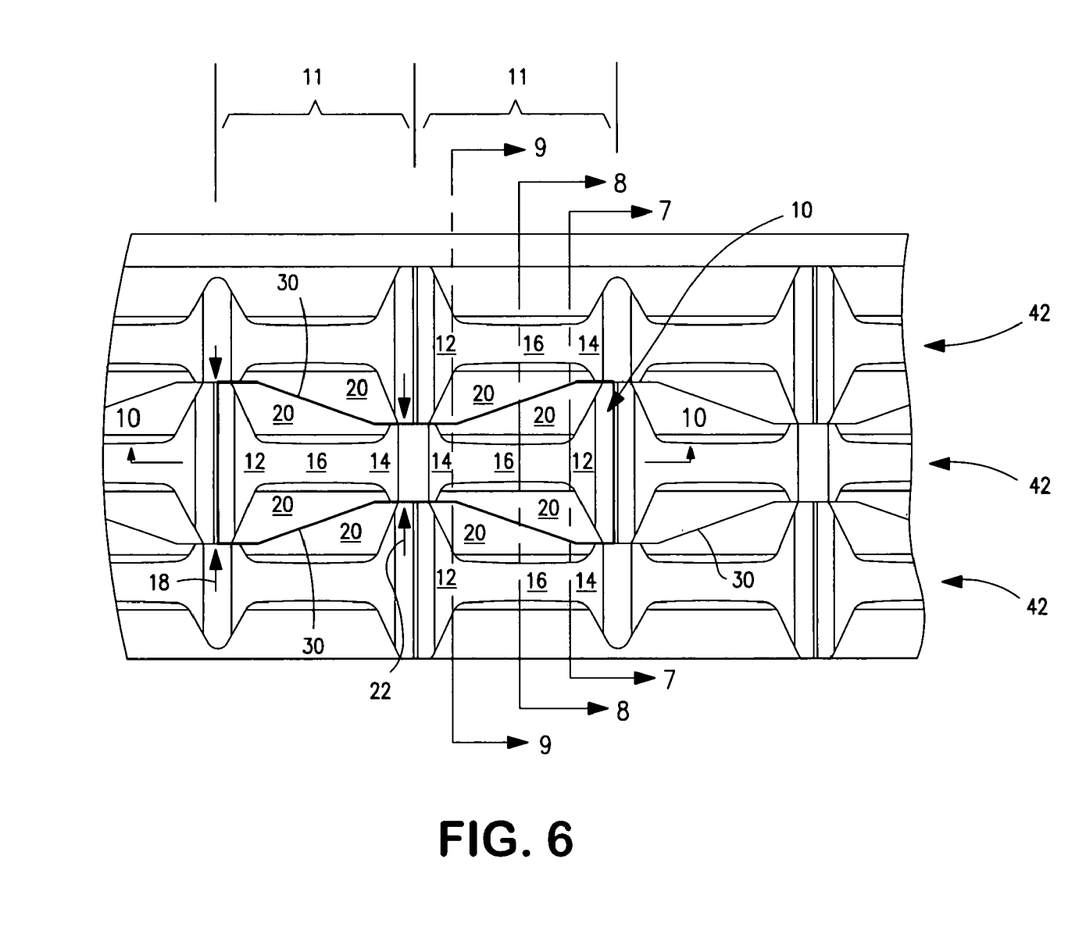
FIG. 6 is an enlarged partial top plan view of a surgical stapler anvil according to aspects of the present invention.
Figure 8:
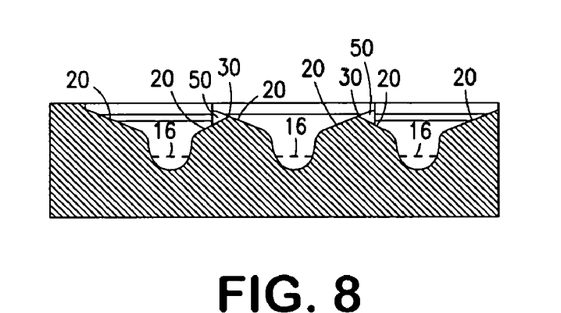
FIG. 8 is a sectional view through the anvil of FIG. 6, taken along line 8—8 thereof.
Figure 11:
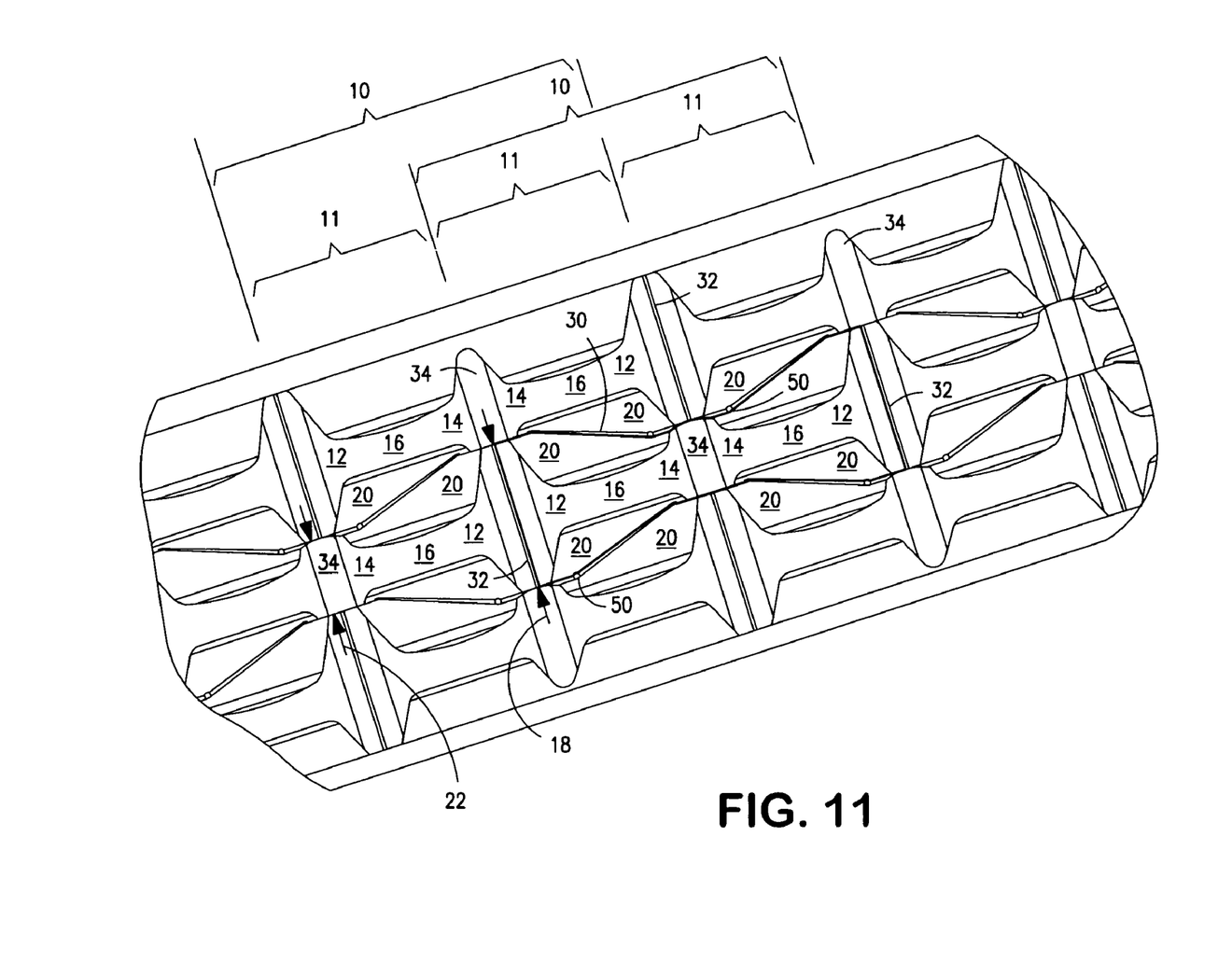
FIG. 11 is a partial overhead perspective view of a surgical stapler anvil according to aspects of the present invention.
Figure 12:
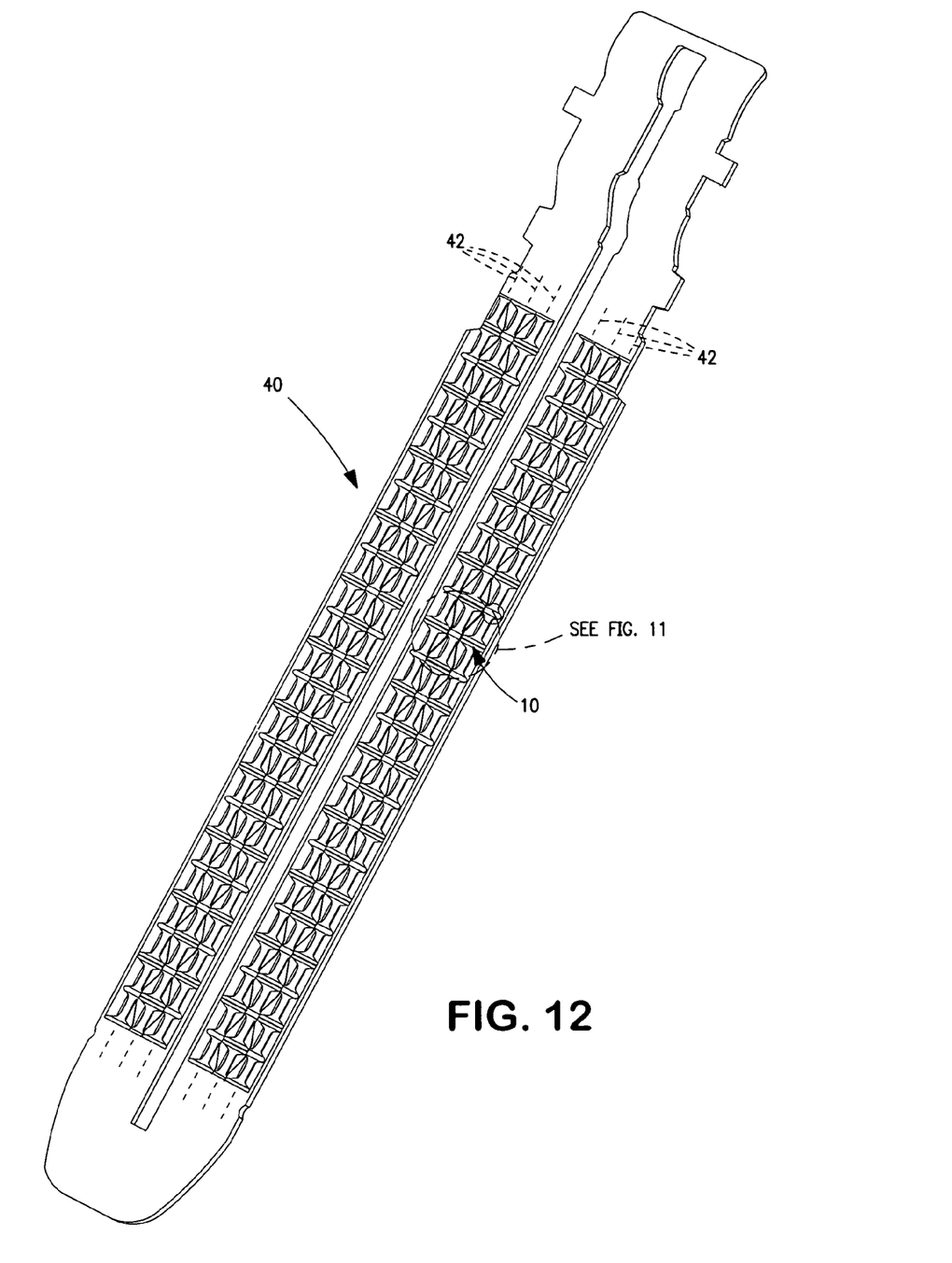
FIG. 12 is a top perspective view of a surgical stapler anvil incorporating nesting pockets according to aspects of the present invention.

FIGS. 6 and 11 are enlarged plan and perspective views, respectively, of a surgical stapler anvil with nested pockets 10 according the aspects of the present invention. Each pocket 10 includes two mirror image leg-forming cups 11. Each leg-forming cup 11 is defined by a concave arcuate clinching surface 16 extending from a descending leg-receiving portion 12 to an ascending leg-clinching portion 14 of the pocket. It will be noted that clinching surfaces 16 are portions of an undulating surface that extends the length of each row 42 of pockets. This undulating, longitudinally extending surface forms the bottom "clinching" surface 16 of each leg-forming cup 11. The clinching surfaces 16 are illustrated as being flat in section. Alternatively, the clinching surfaces may be arcuate in section as shown in FIG. 8. In the context of the present invention, the portion of the clinching surface 16 that is arcuate in section is likely limited to the deepest portion of each leg-forming cup 11.

Figure 7:
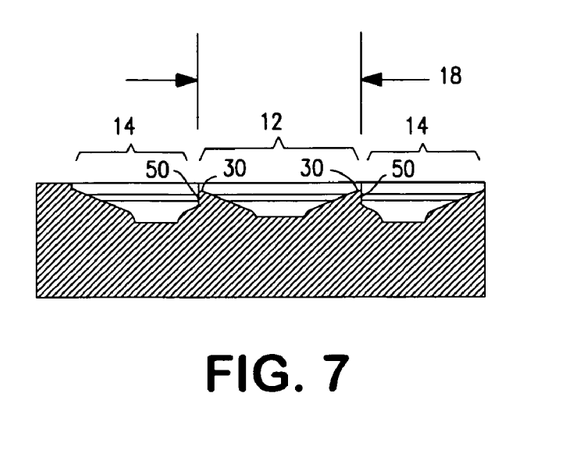
FIG. 7 is a sectional view through the anvil of FIG. 6, taken along line 7—7 thereof.
Figure 9:
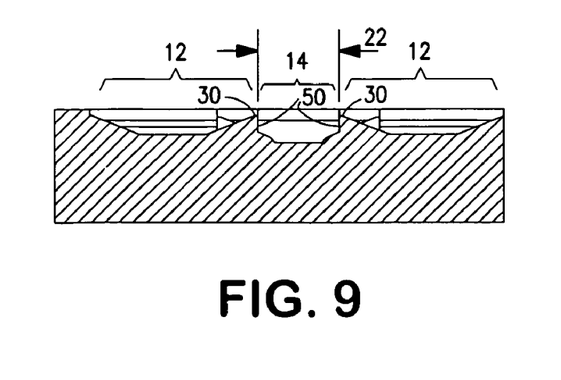
FIG. 9 is a sectional view through the anvil of FIG. 6, taken along along line 9—9 thereof.

Guide surfaces 20 extend upwardly and outwardly from either side of the clinching surface 16. FIGS. 7–9 illustrate the guide surfaces 20 at various points along the pocket 11. The guide surfaces 20 are almost vertical where they join the clinching surface 16 in the deepest part of the cups 11. The guide surfaces 20 flatten out to a shallow angular orientation as they progress laterally outwardly away from the clinching surface 16.

The present invention recognizes that the staggered arrangement of the staple forming pockets presents an opportunity to enlarge the leg receiving portion 12 of the pockets without increasing the lateral spacing between the rows 42 of pockets. This is accomplished according to aspects of the present invention by expanding the lateral width 18 of the leg-receiving portions 12 at the distal ends of each pocket into space that would otherwise be occupied by the leg-clinching portions 14 of a laterally adjacent pocket. The leg-clinching portions 14 do not benefit from added lateral width because the staple leg has already been partially formed and is aligned with the clinching surface 16 prior to arrival at the ascending leg-clinching portion 14 of the pocket.

According to aspects of the present invention the substantially planar laterally outward most portions of the guide surfaces 20 of adjacent rows meet to form a non-linear ridge 30. The ridge traverses a laterally shifting path between the rows 42 of nested pockets 10. FIGS. 7–9 are sectional views through the three parallel rows of nested pockets shown in FIG. 6. FIG. 8 is a sectional view taken through the deepest part of the leg forming cups in three adjacent rows 42. At this position, ridge 30 is approximately equidistant between the leg clinching surfaces 16 of the laterally adjacent cups. Longitudinally, the ridge 30 shifts inwardly and outwardly relative to the length of the rows as best seen in FIGS. 6 and 11. The expanded leg-receiving portion 12 of the pocket in the central row occupies lateral space taken from the leg-clinching portion 14 of the pockets in the adjacent rows. The ridge 30 follows the intersection of the planar laterally outward most portions of the guide surfaces 20. FIG. 9 illustrates the relative positions of the pocket surfaces and ridges 30 at a point closer to the leg-clinching portion 14 of the central pocket and the leg-receiving portions 12 of the laterally outward pockets. It can be seen that the substantially planar guide surfaces of the outward pockets are expanded in the vicinity of their leg receiving portions 12. The ridge 30 is closer to the center of the clinching surface 16 in the vicinity of the leg-clinching portion 14 of the central pocket. FIG. 7 shows the relative positions of the pocket surfaces and ridges 30 at a point closer to the leg-receiving portion 12 of the central pocket and the leg-clinching portions 14 of the laterally outward pockets. In the view of FIG. 7, the guide surfaces 20 of the leg-receiving portion are laterally expanded into the leg-clinching portions 14 of adjacent pockets. The lateral width of each leg-forming cup 11 in the central row of pockets varies from a maximum lateral width 18 at the leg-receiving portion 12 to a smaller lateral width 22 at the leg-clinching portion 14.

Figure 10:
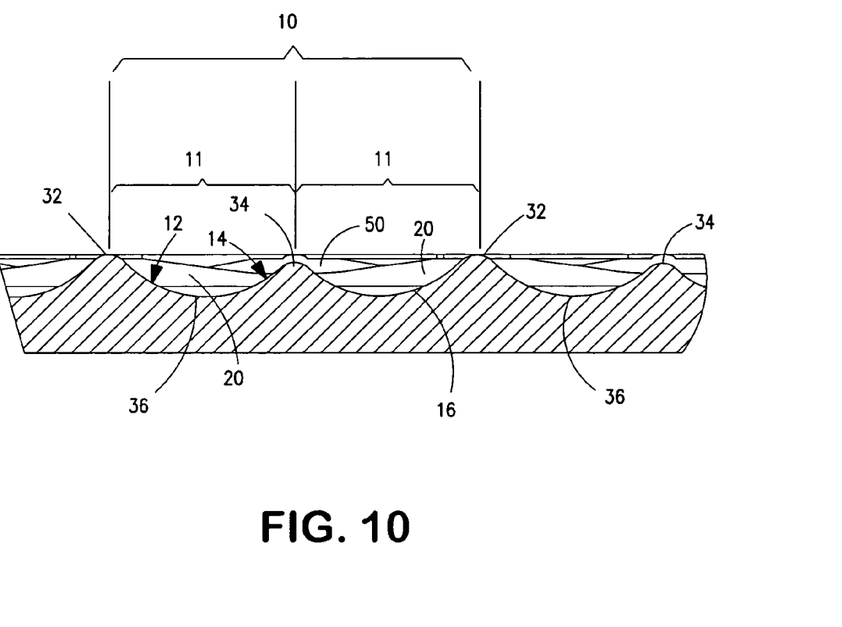
FIG. 10 is a longitudinal sectional view through the anvil of FIG. 6, taken along line 10—10 thereof.

With reference to FIG. 10, the undulating surface of which clinching surfaces 16 are a part is defined by a repeating sequence of three radii of curvature. Clinching surfaces 16 are defined by a radius 36, which repeats along the length of the row of pockets. The bump 34 in the center of each pocket 10 is defined by a radius approximately one-fifth the radius of the clinching surfaces while the slightly higher bumps 32 between pockets are defined by a third radius slightly larger than the radius defining the central bump 34. The central bump 34 may be slightly lower than the bumps 32 between pockets 10 as shown, or may be of substantially the same height. The bumps 32 between pockets form the descending leg-receiving portions 12 of each leg-forming cup 11. With particular reference to FIGS. 10 and 11, the smaller radius, central bumps 34 are laterally adjacent the higher, larger diameter bumps 32 defining the descending leg-receiving portions 12 of adjacent pockets. The formed anvil includes a nearly vertical step 50 extending from the slightly higher lateral edges of a leg-receiving portion 12 down to the lower ascending leg-clinching portion 14 of an adjacent pocket as best seen in FIGS. 7–9. This step 50 vanishes at the longitudinal mid-point of each cup 11 where the planar laterally outward most portions of the guide surfaces 20 are of substantially equal lateral width and height as best seen in FIG. 7.

A preferred method of manufacture for the anvil incorporating nesting pockets is by cold forming or coining using a press to force a die into an anvil blank to form the concave pockets. Each row of pockets is formed by a "blade" having a positive (convex) shape corresponding to the negative (concave) shape of the pockets. The vertical sides of each blade are cut in a pattern corresponding to the laterally shifting ridge 30 at the intersection of laterally adjacent guide surfaces 20. The shaped vertical sides of adjacent blades fit together like puzzle pieces. The blades are clamped in a "chase" which is in turn secured in a press. The clamped, interfitting blades produce the nested three-dimensional pockets when forced into the anvil blank by the press.

Exemplary embodiments of the foregoing invention have been set forth for purposes of illustration. The foregoing description should not be deemed a limitation of the invention herein. Various modifications, adaptations and alternatives may occur to one of skill in the art without departing from the spirit and the scope of the present invention.

What is claimed is:

1. A staple forming anvil having a length and an upper surface defining rows of staple forming pockets parallel to said length comprising:
   first and second substantially identical leg-forming cups defining longitudinally spaced apart descending leg-receiving portions and adjacent ascending leg-clinching portions, each cup comprising:
      a concave arcuate clinching surface extending between said leg-receiving portion and said leg clinching portion; and
      laterally spaced apart guide surfaces extending upwardly and outwardly from said clinching surface, a laterally outward-most portion of said guide surfaces being substantially planar,
   wherein the outward-most portions of laterally adjacent guide surfaces intersect and the leg-receiving portions of at least one row of pockets have a first lateral width that is greater than a second lateral width of the leg-clinching portions of said at least one row of pockets.

2. The staple forming anvil of claim 1, wherein the laterally outward-most portion of said guide surfaces have a substantially equal angular orientation relative to a plane perpendicular to and bisecting said clinching surfaces.

3. The staple forming anvil of claim 1, wherein the laterally outward-most portion of said guide surfaces define an obtuse included angle.

4. The staple forming anvil of claim 3, wherein said obtuse included angle is in the range of 120° to 160°.

5. The staple forming anvil of claim 3, wherein said obtuse included angle is approximately 140°.

6. The staple forming anvil of claim 1, wherein said clinching surface is flat in cross section between said guide surfaces.

7. The staple forming anvil of claim 1, wherein said first lateral width is at least 25% greater than said second lateral width.

8. The staple forming anvil of claim 1, wherein said first lateral width is approximately twice said second lateral width.

9. The staple forming anvil of claim 1, wherein said rows of staple forming pockets are staggered such that the adjacent leg-clinching portions of a pocket in one row are aligned with the leg-receiving portions of staple forming pockets in a laterally adjacent row.

10. The staple forming anvil of claim 1, wherein said rows of staple forming pockets are staggered such that the adjacent leg-clinching portions of a pocket in one row are aligned with the leg-receiving portions of staple forming pockets in a laterally adjacent row and laterally adjacent guide surfaces meet to define a ridge, a major portion of said ridge having an angular orientation to the length of said anvil.

11. The staple forming anvil of claim 1, wherein said rows of staple forming pockets are staggered such that the adjacent leg-clinching portions of a pocket in one row are aligned with the leg-receiving portions of staple forming pockets in a laterally adjacent row and laterally adjacent guide surfaces meet to define a non-linear ridge.

12. In a staple forming anvil of a surgical stapler, the anvil having an upper surface defining a plurality of staple forming pockets in parallel rows, each said pocket comprising:
   first and second leg forming cups each including a descending leg-receiving portion and an ascending leg-clinching portion, said leg-clinching portions being adjacent and said leg-receiving portions being spaced apart, each cup comprising:
      a concave arcuate clinching surface extending between said leg-receiving portion and said leg clinching portion parallel to a longitudinal axis of; anvil; and
      laterally spaced apart guide surfaces extending upwardly and outwardly from said clinching surface, a laterally outward-most portion of said guide surfaces being substantially planar,
   wherein pockets in the parallel rows are staggered so that a leg-receiving portion of a pocket in one row is aligned with a leg-clinching portion of a pocket in an adjacent row, the guide surfaces of adjacent rows intersecting to define a ridge separating the cups of one row from the cups of an adjacent row, the improvement comprising:
   the leg-receiving portions of at least one row of pockets having a lateral width that is at least 25% greater than a lateral width of the leg-clinching portions of pockets in the same row, the increased lateral width of said leg-receiving portions being taken from the leg-clinching portions of cups in an adjacent row.

13. The staple forming anvil of claim 12, wherein said anvil defines a set of three parallel rows of pockets, said at least one row of pockets being a central row of pockets.

14. The staple forming anvil of claim 12, wherein the laterally outward-most portion of said guide surfaces have a substantially equal angular orientation relative to a plane perpendicular to and bisecting said clinching surfaces.

15. The staple forming anvil of claim 12, wherein the intersecting guide surfaces define an obtuse included angle.

16. The staple forming anvil of claim 15, wherein said obtuse included angle is in the range of 120° to 160°.

17. The staple forming anvil of claim 15, wherein said obtuse included angle is approximately 140°.

18. The staple forming anvil of claim 12, wherein said clinching surface is flat in cross section.

19. The staple forming anvil of claim 12, wherein the lateral width of said leg-receiving portions is approximately twice the lateral width of said leg-clinching portions.

20. A staple forming anvil comprising:
a plurality of staple forming pockets arranged in laterally adjacent parallel rows, each said pocket including a pair of longitudinally aligned staple leg-forming cups, each said cup defined by an arcuate clinching surface extending between a descending leg-receiving cup portion and an ascending leg-clinching cup portion and a laterally spaced apart pair of partially planar guide surfaces extending upwardly and outwardly from said clinching surface, said cups arranged with said ascending leg-clinching cup portions abutting each other in a center of each said pocket,
wherein said rows of staple forming pockets are staggered such that the leg-clinching cup portions of a pocket in one row are laterally adjacent to the leg-receiving cup portions of staple forming pockets in an adjacent row and laterally adjacent guide surfaces meet to define a ridge, a major portion of said ridge having an angular orientation to the length of said anvil.

21. The staple forming anvil of claim 20, wherein a major portion of said ridge has an angular orientation relative to the longitudinally aligned staple leg-forming cups.

22. The staple forming anvil of claim 20, wherein said arcuate clinching surface is substantially flat in section.

23. The staple forming anvil of claim 20, wherein said arcuate clinching surface is flat in section over a portion of its length and arcuate in section over a portion of its length.

24. The staple forming anvil of claim 20, wherein the leg-receiving cup portions of at least one row of pockets have a first width measured perpendicular to said longitudinal direction that is at least 25% greater than a second width of said leg-clinching portions.

25. The staple forming anvil of claim 24, wherein said first width is approximately twice said second width.

26. The staple forming anvil of claim 20, wherein said ridge is non-linear.

27. The staple forming anvil of claim 20, wherein said guide surfaces include a laterally outward portion that is substantially planar.

28. The staple forming anvil of claim 21, wherein said guide surfaces include a laterally outward portion that is substantially planar.

29. The staple forming anvil of claim 27, wherein the laterally outward portions of said guide surfaces define an obtuse included angle.

30. The staple forming anvil of claim 20, wherein the leg-receiving cup portion of a pocket in one row has a laterally expanded width that is greater than the leg-clinching cup portion of a pocket in an adjacent row.

\* \* \* \* \*

UNITED STATES PATENT AND TRADEMARK OFFICE
CERTIFICATE OF CORRECTION

| | | |
|---|---|---|
| PATENT NO. | : 6,953,138 B1 | Page 1 of 1 |
| APPLICATION NO. | : 10/782151 | |
| DATED | : October 11, 2005 | |
| INVENTOR(S) | : Dworak et al. | |

It is certified that error appears in the above-identified patent and that said Letters Patent is hereby corrected as shown below:

Column 6:

Line 53, delete "of;" and substitute --of the--.

Signed and Sealed this

Seventeenth Day of October, 2006

JON W. DUDAS
*Director of the United States Patent and Trademark Office*